United States Patent [19]

Drewlow

[11] Patent Number: Plant 6,417

[45] Date of Patent: Nov. 22, 1988

[54] STREPTOCARPUS PLANT NAMED PEGASUS

[75] Inventor: Lyndon W. Drewlow, Ashtabula, Ohio

[73] Assignee: Mikkelsens, Inc., Ashtabula, Ohio

[21] Appl. No.: 9,379

[22] Filed: Jan. 30, 1987

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Schwartz, Jeffery, Schwaab, Mack, Blumenthal & Evans

[57] ABSTRACT

A Streptocarpus plant named Pegasus characterized by its pure white flowers which are long lasting and non-shattering; compact growth habit; ease of propagation; floriferous habit under conditions of both lower light and high temperature, and by its short flexible leaves.

1 Drawing Sheet

The present invention relates to a new and distinct cultivar of Streptocarpus plant, botanically known as *Streptocarpus*×*hybridus*, and known by the cultivar name Pegasus. Pegasus was developed by me through controlled breeding by crossing Mikkelsen Seedling 82-1391-1 (seed parent)×Mikkelsen Seedling 84-770-1 (pollen parent).

Asexual reproduction by me by leaf cuttings has shown that the unique features of this new Streptocarpus are stabilized and are reproduced true to type in successive propagations.

The following characteristics distinguish the new Streptocarpus from both its parent varieties and other cultivated Streptocarpus of this type known and used in the floriculture industry:

1. Pegasus is characterized by its numerous short leaves in a rosette instead of fewer larger leaves such as Snowdrop and other cultivars. The flower stalks are relatively shorter and carried over the foliage, resulting in a cluster of flowers in the middle of green foliage making an attractive 10 cm flowering pot plant. Snowdrop is an unpatented cultivar as is the cultivar Apollo referred to below.

2. Pegasus has a pure white flower while Snowdrop has a yellow eye with creamy white petals. Flower stems on Pegasus are shorter in length than Snowdrop.

3. Pegasus propagates better from leaf cuttings than Snowdrop but not as well as Orion and Janus. Plantlets form in 8 to 10 weeks depending on the season of the year. Orion and Janus are disclosed in pending applications, as are Achilles, Ulyssus, Muse, and Minerva, all referred to below.

4. From a well rooted plant out of a 72 cell pack a well developed flowering plant can be obtained in 6 to 8 weeks which is approximately 10 to 14 days earlier than Snowdrop.

5. Pegasus has shown the ability to tolerate watering with colder than normal (40° F.) water without foliar spotting, and to tolerate fairly high light levels in summer without bronzing or yellowing, traits not found in Snowdrop.

6. Plants of Pegasus are more compact than Snowdrop, Achilles and Ulyssus, and only slightly more compact than Muse.

7. Pegasus has short flexible leaves, and its flowers are long-lasting non-shattering as compared to Snowdrop, Apollo and other older cultivated cultivars, thus making Pegasus an excellent shipping cultivar.

8. Pegasus will flower profusely both under the lower light conditions of winter (December to February) and under the high temperatures of summer (July to September) without going out of bloom under greenhouse conditions. Snowdrop will stop flowering under these conditions.

9. Pegasus is very floriferous when compared to Apollo and Snowdrop due to the large number of flower stalks that develop in each leaf axil on the midrib, and the three flowers per flower stalk.

10. Flower size is similar to Muse and Janus but not as large as Minerva and Ulyssus.

The accompanying color photograph illustrates in perspective view the overall appearance of the cultivar taken as a face view of the plant and showing the colors as true as it is reasonably possible to obtain in a color reproduction of this type.

The following is a detailed description of Pegasus based on plants produced under commercial practices in the greenhouses of Mikkelsens Inc., Ashtabula, Ohio. Color references are made to The Royal Horticultural Society Colour Chart (R.H.S.), except where general colors of ordinary dictionary significance are used.

Classification:

*Botanical.*—*Streptocarpus*×*hybridus*, cv. Pegasus.

Parentage: Controlled cross between Mikkelsen seedling 82-1391-1 and Mikkelsen seedling 84-700-1.

Propagation:

A. *Type cutting.*—Leaf.

B. *Time to develop plantlets.*—*Summer:* 8 weeks at 20° C.; Winter: 10 weeks at 20° C.

C. *Rooting habit.*—Numerous, fine, fibrous.

Plant description:

A. *Form.*—Leaves are rosette, extending from a crown at the soil line with flower stalks forming at the leaf midrib. Many leaves in a symmetrical pattern.

B. *Habit of growth.*—Compact, vigorous, free flowering, never going out of bloom under greenhouse conditions as several flower stalks at various stages of maturity are formed per leaf; flowers carried above foliage.

C. *Height from soil line.*—10 to 12 cm at maturity to top of blooms.

D. *Spread.*—40 to 45 cm at maturity. Leaf Size: 15 to 20 cm in length and 5 to 6 cm in width at the widest point; leaf size can vary greatly with cultural conditions. Quantity: Mature plant can have more than 20 leaves. Leaf Shape: Elliptical. Texture: Lower surface rugose with veins protruding and pubescent; upper surface rugose and pubescent. Margin: Finely crenate. Color: Young foliage top side 146A; under side 148C. Mature foliage top side 137B; under side 148C. Ribs and veins: Pinnate. Rib and vein color: 147C. Leaf tips: Obtuse. Leaf base: Acute.

Flowering description: Flowers open one at a time on the individual flower stalks.

A. *Fully expanded.*—35 to 40 mm.

B. *Stem.*—Single, green in color, approximately 90 mm long, slightly pubescent and round; several develop from a leaf midrib.

C. *Form.*—Funnel shaped in an umbel, with upper two petals reflexed and lower petals flattened to give an overall flat appearance.

D. *Flower bud description.*—18 to 20 mm at maturity, tubular with the end larger in diameter than the rest of bud, 5 green calyx folded over basal end.

E. *Flowers borne.*—In clusters of 2 to 4 flowers per flower stalk, with three being the most common; carried above foliage; pedicels of the flowers in the inflorescence vary in length.

F. *Quantity of flowers.*—Mature plant can have more than 20 flower stalks open, with up to 4 flowers per stalk.

G. *Permanence.*—Long lasting, 10 days or longer.

Color:

A. *Tonality from a distance.*—Pure white with throat same color.

B. *Upper surface of petals.*—155C to D white group.

C. *Under surface of petals.*—155D white group.

D. *Throat.*—155C to D white group.

E. *Discoloration.*—Flowers stay white until drying up when they turn brown.

Petals:

A. *Texture.*—Satin.

B. *Appearance.*—Individually lobed with slight crenate margins; top 2 petals are reflexed and smaller than the 3 bottom petals which are flat.

C. *Arrangement.*—Regularly united into an almost circular shape.

D. *Persistence.*—10 days or longer; petals remain on plant in dry form until picked.

E. *Fragrance.*—None.

Reproductive organs:

A. *Stamens.*—2 fertile. Anther shape: 2 fertile; interconnected and flat. Anther color: Brownish. Filament: Attached to petals for 2 mm and free standing for 5 mm. Pollen color: white.

B. *Pistils.*—Stigma shape: 2 lobed flattened, rounded at end of lobes. Stigma color: White. Stigma size: 2 mm across. Style color: White. Style size: 6 mm. Ovaries: Numerous, 12–15 mm on a receptive pistil, yellow-green.

Disease resistance: No disease problems to date.

Other important characteristics: Compact growth habit combined with the highly floriferous nature makes Pegasus suitable for 10 cm pot plant production. The long lasting and non-shattering flowers and the pliable small leaves of Pegasus facilitate shipping. The pure white flowers do not pink under cool low light conditions. Lack of major disease and insect problems makes for a trouble free crop.

I claim:

1. A new and distinct cultivar of Streptocarpus plant named Pegasus, as illustrated and described, and particularly characterized by its pure white flowers which are long lasting and non-shattering; compact growth habit; ease of propagation; floriferous habit under conditions of both lower light and high temperature, and by its short flexible leaves.

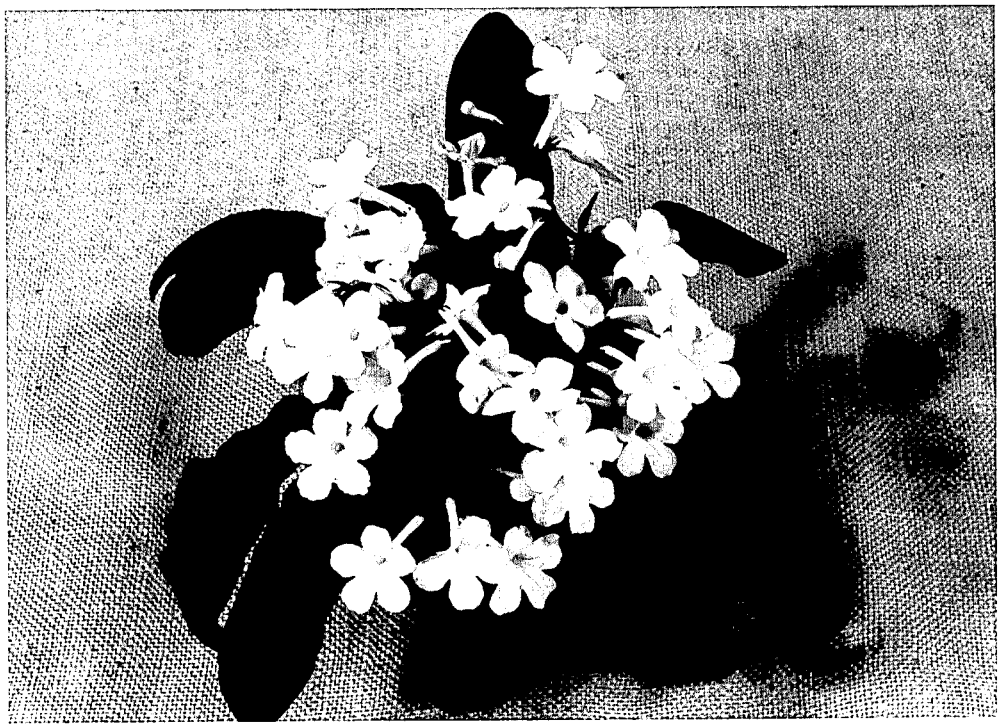

* * * * *